United States Patent [19]

Fike

[11] Patent Number: 5,106,747
[45] Date of Patent: Apr. 21, 1992

[54] METHOD FOR ENZYMATIC REGENERATION OF CELL CULTURE MEDIA AND MEDIA KITS THEREFOR

[75] Inventor: Richard M. Fike, Clarence, N.Y.

[73] Assignee: Life Technologies, Inc., Gaithersburg, Md.

[21] Appl. No.: 593,930

[22] Filed: Oct. 5, 1990

[51] Int. Cl.$^5$ .............................................. C12N 1/38
[52] U.S. Cl. .................................. 435/244; 435/243; 435/69.2; 435/3
[58] Field of Search .................. 435/3, 69.2, 243, 244

[56] References Cited

U.S. PATENT DOCUMENTS 4,891,310  1/1990  Shimizu et al. ........................ 435/3

OTHER PUBLICATIONS

Wandrey Chem. Abstracts, vol. 98, 1983, Abstract #98: 51907g.
Gu. Biomat., Art. Cells & Art Org. 15(1), 297–303 (1987).
Butler, M., *Develop. Biol. Standard.* 60:269–280 (1985).
Chang et al., *Trans. Am. Soc. Artif. Intern. Organs* XXIV:18–20 (1978).
Gu et al., *Biomat., Art. Cells, Art. Org.*, 15(1):297–303 (1987).
Chang and Malouf, *Trans. Am. Soc. Artif. Intern. Organs* 24:18–20 (1978).
Gu and Chang, Applied Biochemistry and Biotechnology, Weetall (Ed.), pp. 115–124, The Humana Press Inc. (1990).
Gu and Chang, *J. Mol. Catalysis* 62:331–339 (1990).
Gu and Chang, *Biotechnol. and Bioengineering* 36:263–269 (1990).
Gu and Chang, *Biotech. Appl. Biochem.* 12:227–236 (1990).

*Primary Examiner*—Douglas W. Robinson
*Assistant Examiner*—Jane A. Williams
*Attorney, Agent, or Firm*—Sterne, Kessler, Goldstein & Fox

[57] ABSTRACT

A multienzyme system capable of reducing waste products and synthesizing nutrients in a cell culture system is disclosed. In one embodiment, lactic dehydrogenase and leucine dehydrogenase are employed in conjunction with amino acid precursors and a recycling co-factor to achieve the synthesis of amino acids and a reduction in the levels of ammonia and lactic acid. The multienzyme system of the invention may be added directly to the cell culture system or it may be microencapsulated. Alternatively, the invention may be utilized in conjunction with a container unit in which cell culture medium contacts the multienzyme system external to the main culture vessel compartment.

24 Claims, 1 Drawing Sheet

METHOD FOR ENZYMATIC REGENERATION OF CELL CULTURE MEDIA AND MEDIA KITS THEREFOR

FIELD OF THE INVENTION

This invention relates to methods of regulating and reducing the build-up of cellular waste products in cell culture systems, with concomitant synthesis of nutrients.

BACKGROUND OF THE INVENTION

Cultured cells catabolize certain nutrients including carbon sources, amino acids, and vitamins. The cells undergo cell division and produce useful cellular products such as monoclonal antibodies, as well as waste products such as ammonia and lactic acid. However, the accumulation of waste products and depletion of nutrients limits the functional life-span of a cell culture. In batch culture, cell death occurs after minimal levels of nutrients have been exhausted and/or intolerable levels of waste products have accumulated. Various solutions to the build-up of waste products and depletion of nutrients have been attempted.

Continuous growth of cultures may be achieved by removing a portion of the culture and replacing it with fresh medium at regular intervals. This serves to remove waste products and replenish needed nutrients. In this method, fluid containing cells and media is continuously withdrawn from the cell culture container and replaced with fresh medium. Alternatively, in a prefusion system cells may be confined to the cell culture vessel such that only medium is withdrawn while fresh medium is added.

However, the components of a cell culture system are not depleted uniformly. Thus, although the perfused media may be depleted of three or four nutrients, it may contain adequate amounts of other components. The removal of these useful components by perfusion is uneconomical.

In these various systems, nutrient and waste levels are maintained by withdrawing "spent" medium and replacing with fresh medium. However, especially in large scale/high density cultures, perfusion of nutrients requires the costly transfer of large volumes of media from the manufacturer to the culture facility, into the bioreactor, and finally to the product isolation facility. One way to minimize the cost and inconvenience of shipping large volumes of media is by the use of concentrates of tissue culture media. However, concentrates need to be reconstituted with water prior to addition to the cultures and large volumes of spent media are generated.

Perfusion is associated with other disadvantages. For example, perfusion systems are susceptible to plugging by cells which must be separated from spent culture media. This is a significant concern for high density cultures since prodigious amount of fluids must be exchanged, sometimes greater than one culture volume per day. In addition, cell products must be isolated from the large volumes of spent culture media generated, and after products are isolated, large volumes of spent culture media must be disposed of.

Absorption technology has been advocated for removal of the waste product ammonia (Gordon, A., Greenbaum, M., Marantz, L., MacArthur, M. and Maxwell, M., "A Sorbent Based Low Volume Recirculating Dialysate System", Trans. Amer. Soc. Artif. Int. Organs 15:347-352, 1969)). Although this system eliminates ammonia, nutrient levels are not affected. In addition, in-place regeneration of the adsorptive agent, zirconium phosphate, is difficult after the agent is saturated with ammonia. Reverse osmosis systems again offer only toxin reduction capabilities with no means of increasing nutrient levels.

Thus, it would be an obvious benefit to the practice of cell culture if nutrients and waste products could be maintained within desired levels without the need for perfusion of large volumes of media.

SUMMARY OF THE INVENTION

According to the invention, a multienzyme system permits the synthesis of nutrients, such as amino acids, and reduction of waste products, such as ammonia and lactic acid in cell culture systems. In a preferred embodiment, lactate dehydrogenase converts lactate to pyruvate in the presence of the co-factor $NAD^+$. Leucine dehydrogenase converts α-keto acids to corresponding amino acids in the presence of NADH, which is generated by the lactate dehydrogenase reaction. The co-factor recycles continuously in the presence of adequate levels of substrates.

The present invention provides a mechanism for converting deleterious waste products into nutrients otherwise depleted in the cell culture system. It can be applied to systems for maintaining the levels of amino acids and other components necessary for continuous growth of cells in culture. As a result, the productive life-span of cultured cells is prolonged.

BRIEF DESCRIPTION OF THE FIGURE

FIG. 1 illustrates a representative multienzyme system.

DETAILED DESCRIPTION OF THE INVENTION

Figure 1:
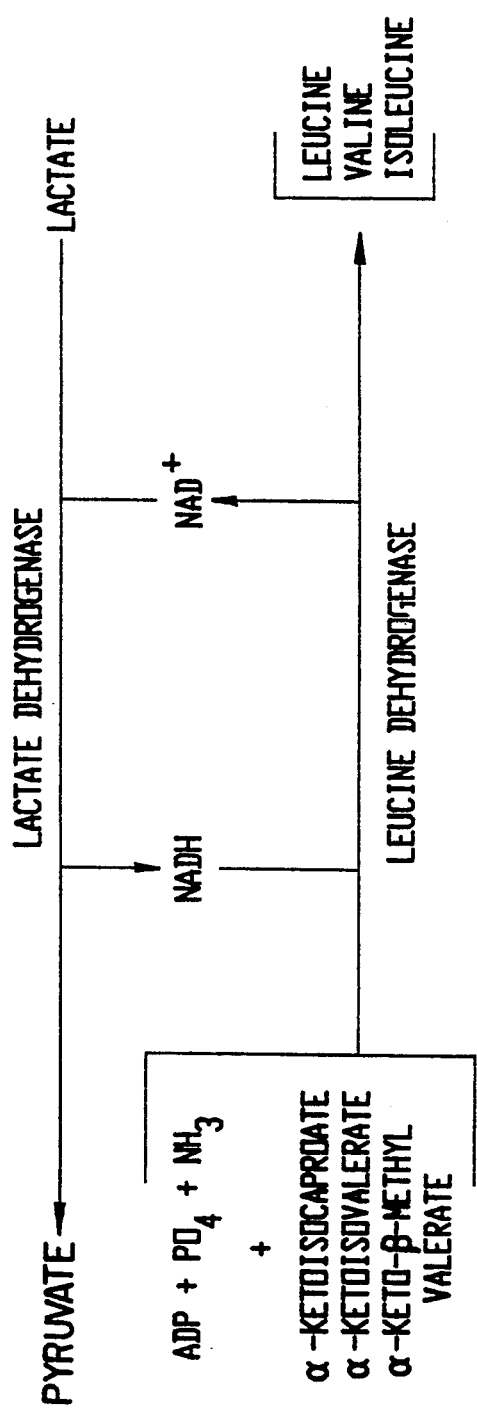
FIG. 1.

According to the invention, a reduction in waste products and a concomitant synthesis of amino acids and/or other nutrients in a cell culture system can be achieved using a multienzyme system.

By "cell culture system" is meant a system of growing cells in vitro in a culture vessel. Although the system is not limited to any particular culture vessel configuration or cell type, in a preferred embodiment, mammalian cells are grown in liquid culture media.

By "contacting," in reference to the cell culture medium, is meant the exposure of cell culture medium to the multienzyme system of the invention such that the enzymes of the multienzyme system (a) catalyze reactions between at least one component of the medium, such as a waste product, and a component of the multienzyme system, such as an amino acid precursor, and (b) regenerate the recycling co-factor of the multienzyme system.

By "recycling co-factor" is meant a nonprotein substance essential for activity of an enzyme. In one embodiment of the present invention, nicotinamide adenine dinucleotide ($NAD^+$) is a co-factor. $NAD^+$ is capable of conversion to NADH by electron transfer.

In one embodiment of the invention, $NAD^+$ is generated by the action of leucine dehydrogenase on an amino acid precursor to form an amino acid. Lactic dehydrogenase converts lactate to pyruvate, and by this reaction regenerates the co-factor as NADH.

By "nutrient" is meant any biological compound essential for growth and/or division of cells in culture. In one embodiment of this invention, amino acids are nutrients. Non-amino acid compounds, such as pyruvate, are also nutrients.

By "nutrient precursor" is meant a compound capable of enzymatic conversion into a nutrient. In one embodiment of this invention, the amino acid precursors α-ketoisocaproate, α-ketoisovalerate and α-keto-β-methylvalerate are precursors of, respectively, leucine, valine and isoleucine. One or more of these precursors can be employed in the multi-enzyme system.

By "multienzyme system" is meant a plurality of cooperatively functioning biological components capable of achieving the synthesis of at least one nutrient, utilizing at least one waste product and at least one nutrient precursor. According to a preferred embodiment, the multienzyme system of this invention contains lactate dehydrogenase, leucine dehydrogenase, ADP, KCl, NAD+, α-ketoisocaproate, α-ketoisovalerate and α-keto-β-methylvalerate.

Enzymes useful in the multienzyme system of the invention can be tested and selected on the basis of the following eight factors:

1) Toxicity and required concentrations of enzymes and co-factors. At working concentrations, the required molecules must not be toxic or inhibitory to cell growth and/or to the synthesis of biological products of the cells.

2) Enzyme activity in cell culture media. Some enzymes are known to be inhibited by various amino acids which are major components of cell culture media.

3) The preferred species and isotype of the various enzymes. It is well known that enzymes from different species, as well as isotypes within a species, vary in their affinity for different substrates. For example, lactic dehydrogenases from beef heart exist in four forms, each having a different affinity for lactate. These affinities differ from the affinity of skeletal muscle lactic dehydrogenase, for which pyruvate is the preferred substrate. Also, glutamine synthetase from sheep brain is less likely to be inhibited by amino acids than that from bacterial sources (*Meth. Enzymol.* 113: Section II (Glutamine), 1985).

4) Inactivation of enzyme systems by proteases and other components of the cell culture system. Numerous proteolytic and inhibitory molecules may be likely to affect enzyme performance in a cell culture system, especially at high density.

5) Physiological environment is important. Many mammalian cell cultures require media of essentially neutral pH and temperatures of 37°±2° C., a point at which many native enzymes are unstable.

6) Priming concentrations of ammonia/lactate. These concentrations must be compatible with the cell culture system.

7) Sterilization of materials for microencapsulation. For use in a cell culture system, all components and phases of the microencapsulation process must be sterile.

8) The effect of reaction kinetics. The reaction of pyruvate to lactate is thermodynamically favored. This is not desired in cell culture.

One method of selecting a particular enzyme for use in the multienzyme system is to first identify in a cell culture the accumulation of an undesirable waste product. Once this product is identified, enzymes are selected that will convert the waste product into another form, preferably a nutrient source for the cell culture. The enzymes may be used in combination with an appropriate co-factor, preferably a co-factor capable of continuously recycling in the presence of adequate levels of substrates. The identity of the co-factor will be determined by the requirements of the enzymes chosen and their particular substrates.

A representative multienzyme system is illustrated in FIG. 1. This system meets the requirements enumerated above for use in a cell culture system.

In a preferred embodiment, the system employs two enzymes, lactic dehydrogenase and leucine dehydrogenase, and a recycling co-factor (NAD+/NADH). Lactate dehydrogenase converts lactate to pyruvate in the presence of NAD+. Leucine dehydrogenase converts α-ketoacids (α-ketoisocaproate, α-ketoisovalerate, and α-keto-β-methyl valerate) into corresponding amino acids (leucine, valine, and isoleucine, respectively) in the presence of NADH, which is generated by the lactate dehydrogenase reaction. The co-factor recycles continuously as long as adequate levels of lactate, ammonia, and an amino acid precursor are present.

In a cell culture, the multienzyme system achieves the synthesis of amino acids with concomitant decreases in the waste products ammonia and lactic acid.

In other embodiments, alanine can be produced by the reductive amination of pyruvate, and glutamine can be produced from glutamic acid by the action of glutamine synthetase.

The form of the invention is not limited to a soluble solution or microencapsulated enzymes. The invention can be utilized in conjunction with a container unit, wherein some or all of the cell culture medium is exposed to the multienzyme system within the container. For example, the multienzyme system can be placed within a hollow fiber unit, within a compartment separated by a semipermeable membrane. Cell culture (media and cells) passes through the center of the hollow fibers, and waste products from the media diffuse across the semipermeable membrane to contact the enzyme system. The waste products are converted into nutrients, such as amino acids, by the action of the multienzyme system, and these nutrients pass through the membrane to the cell culture.

In such a system, continuous automatically adjusted operation is possible. As the levels of waste products increase, the multienzyme system is triggered, whereas the multienzyme system is relatively inactive when waste products are at a low concentration, such as at the start of a new cell culture.

The container unit may be included as a component of a kit for convenient use with a cell culture system. The container unit of the kit may contain the enzymes of the multienzyme system. Other compartments of the multienzyme system, specifically a nutrient precursor and a recycling co-factor, can be supplied separately. The kit would also provide a means for contacting the cell culture with the multienzyme system. Optionally, the kit also provides a container having cell culture medium.

In one embodiment of the kit, the container means is a hollow fiber unit, and the enzymes are contained within a first compartment. One or more nutrient precursors and a recycling co-factor are added to the compartment containing the enzymes. The cell culture is contacted with the multienzyme system through a second compartment which is separated from the first compartment by the semi-permeable membrane. The second compartment receives cell culture media, or media and cells, from the main culture vessel through, for example, a hollow tube.

In other embodiments of the kit, the first compartment of the container unit may contain the enzymes of the multienzyme system, and, in addition, one or more nutrient precursors and/or a recycling cofactor.

In another embodiment of the kit, separate containers are provided which hold, respectively, enzymes, co-factor(s) and nutrient precursors. Optionally, the enzymes may be provided in a microencapsulated form. The components are added to the culture system when appropriate on the basis of the growth conditions of the culture.

One of skill in the art of cell culture is familiar with the various mechanical systems associated with maintaining cell cultures. According to the invention, the multienzyme system can be conveniently incorporated into virtually any cell culture system. However, the invention is not intended to be limited to use with known cell culture systems, and it is envisioned that as new and improved mechanical cell culture systems and apparatus are developed, spent cell culture media can be regenerated using the multienzyme system of the invention.

The following examples describe the application of non-microencapsulated and microencapsulated multienzyme systems to cell culture systems.

EXAMPLE 1

General Methods. The following enzymes and cofactors are added to a cell culture system, in the order presented:
A. Add lactic dehydrogenase to tissue culture medium.
B. Reconstitute leucine dehydrogenase with "A".
C. Add $NAD^+$ to "B".
D. Add ADP to "C".
E. Add KCl to "D".
F. Add $\alpha$-ketoisocaproate, $\alpha$-ketoisovalerate and $\alpha$-keto-$\beta$-methyl valerate to "E".
G. Filter "E" through a 0.22$\mu$ non-pyrogenic Duropore membrane (Millipore Corp., Bedford, Mass. 01730).
H. Store at 2°–4° C. until further use.

It is possible to either add the above reagents directly to the tissue culture medium for use or to formulate this as a concentrate in tissue culture medium which is then diluted into tissue culture media to provide the indicated final concentrations. (This may be desired if several types of cells or conditions are to be tested simultaneously.) It is also possible to adjust concentrations of reactants depending upon cell type, the desired rate of depletion of culture nutrients, and the rate of generation of waste products.

EXAMPLE 2

Microencapsulation of Enzyme Systems

Reagents

A) Hexanediamine Solution
1. Add 0.378 g of $NaHCO_3$ to 5 ml deionized water.
2. Add 0.464 g of 1,6-hexanediamine and dissolve.
3. Adjust pH to 9.0 with 5N HCl.
4. Add 2 ml of 50% polyethyleneimine.
5. Mix by inversion and re-adjust pH to 9.0.
6. Adjust volume to 10 ml with deionized water.
7. Filter through 0.22 $\mu$ Duropore membrane.
8. Store at 2°–4° C.
B) Organic Solvent 1. Mix 12 ml chloroform with 48 ml cyclohexane (1:4 v/v of chloroform: cyclohexane).
2. Add 0.9 ml Span 85 (Sorbitan Trioleate, Sigma Chemical Co., St. Louis, Mo.)
3. Filter through 0.2 $\mu$ pore size Acrodisc CR (Gelman, sterilize by autoclaving).
4. Prepare fresh daily.
5. Store at 2° C.–4° C.
C) Terephthaloyl Chloride Solution
1. Add 55 mg of terephthaloyl chloride to 15 ml organic solvent. Stir (or agitate gently) on ice for 30 minutes to dissolve.
2. Filter through 0.2 $\mu$ pore size Acrodisc CR (Gelman, sterilize by autoclaving).
D) Tween-20 Solution (50%)
Dilute Tween-20 with equal volume of deionized, distilled $H_2O$. Adjust pH to 7.5 with 5N NaOH. Autoclave to sterilize. All glassware, (e.g. centrifuge tubes, flasks with covers, glass syringes, pipettes, etc.) must be autoclaved prior to use.

Procedure

1. Add lactic dehydrogenase to tissue culture medium (see Table 1).
2. Reconstitute leucine dehydrogenase with (1).
3. Filter sterilize (0.22 $\mu$ Duropore membrane).
4. Under sterile conditions, mix equal volumes of (3) with hexanediamine solution. Keep on ice.
5. Vortex (vigorously) to emulsify, and while vortexing, add 15 ml of organic solvent. (Use 125 ml Erlenmeyer flask with cover).
6. Continue vortexing for one minute.
7. After one minute, add 15 ml of Terephthaloyl chloride solution. Continue vortexing for three minutes more.
8. After three minutes, add 30 ml organic solvent. Vortex 30 seconds.
9. Pour microcapsules into sterile glass centrifuge tube. Centrifuge at 1000 RPM for 2.5 minutes.
10. Discard supernatant under sterile conditions. Add 25 ml of 50% Tween 20, pH 7.5. Vortex to mix. Add 50 ml sterile deionized water, vortex and centrifuge at 2500 RPM for five minutes.
11. Wash several times with PBS.
12. Store at 4° C. until use.
13. Prior to use, wash twice with media of choice for cell culture.
14. Example: 1.5 ml of enzyme solution (Step "2") yields approximately 3–4 ml of microcapsules which is sufficient to add to 15 ml of cell culture.
15. After the cell culture, (see below) and enzyme solution have been mixed together, the remaining components of the enzyme system need to be added, (i.e. $NAD^+$, ADP, KCl, and the $\alpha$-ketoacids). These may be added as concentrates (see chart) to the microencapsulated enzyme-cell culture mixture.

EXAMPLE 3

Cell Culture Specifications

Use of enzyme regenerative technology has most relevance and utility at high cell densities where waste products are elevated, yielding triggering concentrations of ammonia and lactic acid. Also at higher cell densities, less enzyme is required for a given unit/ml concentration. For hybridoma cells, good results have been observed with cells plated at $10^7$/ml. At this concentration, agitation is necessary to keep cells from clumping, as well as to assure adequate oxygenation. Cells may be cultured in a bioreactor (oxygen, pH-controlled) with impeller design or in 12 well trays.

1) Cells should have viabilities greater than 90% and be in late log phase. It is preferable to avoid lag-phase cells.
2) Perform cell counts and adjust volume to contain $10^7$ cells/ml.
3) It is preferable to supplement glutamine into the basal media at a 3x (6 mM) concentration (for a total of 8 mM) to avoid glutamine insufficiency.
4) Prepare concentrates of $NAD^+$, α-ketoacids, ADP, and KCl according to Table 1.
5) Prepare enzymes in tissue culture media, following steps A–H of Example 1.
6) Centrifuge cells and resuspend in tissue culture media. In order to have a final concentration of $1 \times 10^7$ cells/ml, it is important to take into account the dilution upon addition of the enzyme mixture (step 8).
7) Add cells to culture vessel or tray.
8) Immediately add enzyme mixture, $NAD^+$, α-ketoacids, ADP and KCl. It is preferable to avoid alkaline conditions.
9) Place culture vessel or tray within a humidified chamber containing 5–10% $CO_2$/90%–95% air. This chamber may be placed upon a rotator at approximately 150 RPM.
10) Incubate at 37° C.
11) Daily samples for determination of glucose, lactic acid, ammonia, viability, amino acid content and production capability (e.g. monoclonal antibody) should be performed.

Results

Table 2 illustrates the synthesis of amino acids in a PBS aqueous phase (no cells) over 168 hours. As can be seen, isoleucine, leucine and valine increased significantly over this time period.

Tables 3 and 4 illustrate production levels of synthesized amino acids produced in a pH and oxygen-controlled bioreactor at high cell density, with enzymes free in solution (Table 3) and microencapsulated (Table 4). Both experiments demonstrate that amino acid levels were increased by enzymatic means in cell culture and that microencapsulation is a viable alternative for separating enzymes from the cellular milieu.

Tables 5 and 6 illustrate the results of a high density 12 well tray assay. The presence of the enzyme mixture correlated with significantly higher cellular viability, monoclonal antibody production and less ammonia and lactic acid than without the enzyme mixture. The data illustrate that amino acid levels, as well as concentrations of lactic acid and ammonia, correlated with viability and monoclonal antibody production.

I. Levels of Amino Acids (Table 5)

Levels of isoleucine, leucine and valine, the synthesis of which is catalyzed by leucine dehydrogenase, are significantly elevated in all enzyme-containing cultures and media at all dilutions of enzyme tested (both skeletal muscle and bovine heart lactic dehydrogenase) compared to cultures lacking the enzyme system. Levels of these amino acids in cultures not containing the enzyme system are essentially depleted.

II. Levels of Ammonia/Lactic Acid (Table 6)

Levels of ammonia and lactic acid in most cultures were decreased in the presence of enzyme systems compared to cultures with no enzyme system. (The enzyme system was found to need titration to reach proper levels for lactate control relative to non-enzyme containing cultures). Ammonia levels are observed to correlate quite closely with monoclonal antibody levels (see Table 6).

III. Cellular Viability (Table 6)

Appropriate enzyme systems could be found to significantly increase viability compared to non-enzyme containing cultures (e.g., skeletal muscle LDH/PFHM-II). Skeletal muscle LDH/RPMI-1640+GMS-X and bovine heart LDH with PFHM-II also gave improved viability in culture.

IV. Monoclonal Antibody Production (Table 6)

The most important aspect to industry of a cell culture system is the affect on cellular production. As can be seen, the presence of properly titered enzyme systems in each category correlated with significant improvement in monoclonal antibody production.

TABLE 1

| FORMULATION OF A MULTIENZYME SYSTEM | | | |
|---|---|---|---|
| Item | Source/Type | Final Concentration in Cell Culture | Comments(s) |
| Leucine Dehydrogenase | Bacillus Species | 1.25 units*/ml | Reconstitute lyophilized enzyme directly with media at 1:10 (wt.:vol.) in PBS. |
| L-Lactic Dehydrogenase | Bovine Heart Muscle LDH-1 ($H_4$) or Rabbit Muscle Type XXXIX | 17.5 units**/ml | 1:5 (media) to 1:50 (PBS) concentrate. |
| α-ketoacids | α-ketoisocaproate α-Ketoisovalerate α-Keto-β-Methyl Valerate | 0.5 mg/ml | Add powder directly to media or prepare 100x in PBS. |
| $NAD^+$ (β-NAD) β-Nicotinamide Adenine Dinucleotide | Grade III, approx. 98%, from yeast | 1.3 μg/ml | 1:100–1:500 (PBS) concentrate. |
| ADP (Adenosine 5'-Diphosphate) | Sodium salt, Grade III, 95–99%, from yeast ATP | 10 μg/ml | 1:100–1:500 (PBS) concentrate. |
| KCl | Certified ACS | 77 μg/ml | 1:100–1:500 (PBS) concentrate. |

*One unit converts 1.0 μmole of L-leucine to α-ketoisocaproate per minute at pH 10.5 at 37° C.
**One unit reduces 1.0 μmole of pyruvate to L-lactate per minute at pH 7.5 at 37° C.

TABLE 2

TIME COURSE OF SYNTHESIS OF VALINE, ISOLEUCINE AND LEUCINE IN PBS WITH NO CELLS AT ROOM TEMPERATRURE

| Amino Acid | Amino Acid Concentrations (mg/l) | | | | | |
|---|---|---|---|---|---|---|
| | 15 min | 14.5 Hr | 24 hr | 63 hr | 137 hr | 165 hr |
| Valine | 76 | 353 | 477 | 759 | 1048 | 1106 |
| Isoleucine | 73 | 351 | 477 | 773 | 1114 | 1197 |
| Leucine | 124 | 567 | 722 | 1067 | 1456 | 1551 |

TABLE 4

LEVELS (MG/L) OF VALINE, ISOLEUCINE AND LEUCINE IN A pH/$O_2$-CONTROLLED BIOREACTOR AT HIGH CELL DENSITY ($10^7$ AE-1 HYBRIDOMA CELLS/ML) WITH MICROENCAPSULATED ENZYMES

| Amino Acid | Control | +E (24 Hrs) | −E (24 Hrs) | +E (48 Hrs) | −E (48 Hrs) |
|---|---|---|---|---|---|
| Valine | 156 | 304 | 90 | 452 | 92 |
| Isoleucine | 154 | 231 | 46 | 337 | 34 |
| Leucine | 308 | 409 | 120 | 560 | 98 |

TABLE 5

PROFILE OF AMINO ACIDS (MG/L) SIGNIFICANTLY ALTERED DURING HIGH DENSITY CELL CULTURE

| Test | Alanine | Cystine | Glycine | Glutamine | Isoleucine | Leucine | Methionine | Valine |
|---|---|---|---|---|---|---|---|---|
| A | 31 | 10 | 651 | 2 | 162 | 119 | 5 | 158 |
| B | 33 | 0 | 602 | 1 | 169 | 130 | 4 | 167 |
| C | 36 | 0 | 538 | 1 | 166 | 142 | 3 | 171 |
| D | 492 | 15 | 461 | 1 | 7 | 25 | 7 | 23 |
| E | 17 | 0 | 412 | 1 | 216 | 252 | 0 | 216 |
| F | 18 | 0 | 436 | 0 | 216 | 201 | 0 | 204 |
| G | 18 | 0 | 432 | 0 | 187 | 175 | 0 | 175 |
| H | 130 | 0 | 412 | 1 | 4 | 12 | 0 | 7 |
| I | 366 | 18 | 132 | 638 | 153 | 286 | 59 | 239 |
| J | 151 | 0 | 531 | 1 | 170 | 189 | 5 | 188 |
| K | 106 | 0 | 508 | 1 | 155 | 158 | 3 | 174 |
| L | 884 | 0 | 399 | 1 | 12 | 41 | 12 | 36 |
| M | 150 | 13 | 157 | 9 | 228 | 267 | 5 | 234 |
| N | 29 | 0 | 344 | 1 | 213 | 199 | 0 | 202 |
| O | 26 | 0 | 350 | 1 | 208 | 203 | 0 | 196 |
| P | 295 | 0 | 314 | 1 | 5 | 15 | 0 | 3 |
| Q (PFHM-II Control) | 411 | 78 | 10 | 964 | 133 | 325 | 73 | 145 |
| R (RPMI-1640 + GMS-X Control) | 0 | 55 | 9 | 1000 | 41 | 48 | 9 | 19 |

TABLE 6

HIGH DENSITY CELL CULTURE ASSAY RESULTS (96 HRS. EXCEPT AS NOTED)

| Test | Enzyme System Dilution | Source of Lactic Dehydrogenase | Medium | % Viability (*24 hrs.) (**48 hrs.) | Lactate (g/L) | Glucose (g/L) | $NH_3$ (mM) | Mab (ug/ml) |
|---|---|---|---|---|---|---|---|---|
| A | 0 | Skeletal Muscle | PFHM-II | 82** | 0.05 | 0.55 | 6.22 | 260 |
| B | 1:5 | Skeletal Muscle | PFHM-II | 82** | 0.05 | 0.45 | 6.23 | 254 |
| C | 1:10 | Skeletal Muscle | PFHM-II | 70** | 0.05 | 0.50 | 6.85 | 216 |
| D | — | — | PFHM-II | 28** | 0.10 | 0.50 | 6.90 | 179 |
| E | 0 | Skeletal Muscle | RPMI-1640 + GMS-X | 37** | 0.05 | 0.45 | 3.61 | 185 |
| F | 1:5 | Skeletal Muscle | RPMI-1640 + GMS-X | 52** | 0.10 | 0.55 | 4.22 | 168 |
| G | 1:10 | Skeletal Muscle | RPMI-1640 + GMS-X | 48** | 0.05 | 0.35 | 4.36 | 136 |
| H | — | — | RPMI-1640 + GMS-X | 46** | 0.10 | 0.55 | 5.99 | 143 |
| I | 0 | Bovine Heart | PFHM-II | 2* | 1.85 | 0.65 | 19.6 | 47 |
| J | 1:5 | Bovine Heart | PFHM-II | 96* | 0.05 | 0.55 | 7.96 | 294 |
| K | 1:10 | Bovine Heart | PFHM-II | 94* | 0.05 | 0.30 | 7.64 | 309 |
| L | — | — | PFHM-II | 86* | 0.10 | 0.50 | 16.9 | 167 |
| M | 0 | Bovine Heart | RPMI-1640 + GMS-X | 25** | 0.75 | 0.50 | 20.5 | 59 |
| N | 1:5 | Bovine Heart | RPMI-1640 + GMS-X | 0** | 0.05 | 0.40 | 6.2 | 151 |
| O | 1:10 | Bovine Heart | RPMI-1640 + GMS-X | 27** | 0.05 | 0.50 | 5.4 | 182 |
| P | — | — | RPMI-1640 + GMS-X | 37** | 0.10 | 0.60 | 15.5 | 102 |

TABLE 3

LEVELS (MG/L) OF VALINE, ISOLEUCINE AND LEUCINE IN A pH/$O_2$-CONTROLLED BIOREACTOR AT HIGH CELL DENSITY ($10^7$ AE-1 HYBRIDOMA CELLS/ML) ENZYMES FREE IN SUSPENSION

| Amino Acid | Control | +E (24 Hrs) | −E (24 Hrs) | +E (48 Hrs) | −E (48 Hrs) |
|---|---|---|---|---|---|
| Valine | 153 | 312 | 59 | 559 | 32 |
| Isoleucine | 156 | 226 | 22 | 473 | 2 |
| Leucine | 319 | 387 | 70 | 626 | 19 |

Although the present invention has been described in connection with preferred embodiments, it is understood that modifications and variations are contemplated that do not depart from the spirit and scope of the invention. Such modifications and variations are considered to be within the scope of the invention and the appended claims.

We claim:

1. A method for controlling the concentration of ammonia in a cell culture system, comprising adding to said cell culture system an amino acid precursor, a first enzyme capable of catalyzing the reaction between ammonia and said amino acid precursor to give an amino acid, a recycling cofactor, and a second enzyme capable of regenerating said cofactor.

2. The method of claim 1, wherein said amino acid precursor is selected from the group consisting of α-ketoisocaproate, α-ketoisovalerate, and α-keto-β-methylvalerate.

3. The method of claim 1, wherein said first enzyme is leucine dehydrogenase.

4. The method of claim 1, wherein said recycling cofactor is NAD+.

5. The method of claim 1, further comprising adding to said cell culture system adenosine diphosphate.

6. The method of claim 1, wherein said first and second enzymes are added to said cell culture system in microencapsulated form.

7. A method for controlling the concentration of ammonia in a cell culture system, comprising adding to said cell culture system leucine dehydrogenase, NAD+, adenosine diphosphate and an amino acid precursor selected from the group consisting of α-ketoisocaproate, α-ketoisovalerate, and α-keto-β-methylvalerate.

8. A method for controlling the concentration of lactate in a cell culture system, said method comprising adding to said cell culture system lactate dehydrogenase, NAD+ and leucine dehydrogenase.

9. A method for controlling the concentration of ammonia and lactate in a cell culture system, said method comprising adding to said cell culture system an amino acid precursor, a first enzyme capable of catalyzing the reaction between said ammonia and said amino acid precursor to give an amino acid, NAD+, and a second enzyme capable of regenerating said NAD+ and dehydrogenating lactate to give pyruvate.

10. The method of claim 9, wherein said amino acid precursor is selected from the group consisting of α-ketoisocaproate, α-ketoisovalerate, and α-keto-β-methylvalerate.

11. A method of regenerating cell culture media, wherein said media contains ammonia, said method comprising adding to said cell culture media an amino acid precursor, a first enzyme capable of catalyzing the reaction between said amino acid precursor and ammonia to give an amino acid, a recycling cofactor, and a second enzyme capable of regenerating said cofactor.

12. The method of claim 11, wherein said amino acid precursor is selected from the group consisting of α-ketoisocaproate, α-ketoisovalerate, and α-keto-β-methylvalerate.

13. The method of claim 11, wherein said recycling cofactor is NAD+.

14. The method of claim 11, wherein said second enzyme is lactic hydrogenase.

15. The method of claim 11, further comprising adding to said cell culture system adenosine diphosphate.

16. The method of claim 11, wherein said first and second enzymes are added to said cell culture system in microencapsulated form.

17. A method of regenerating cell culture media, wherein said media contains lactate, said method comprising adding to said cell culture media lactate dehydrogenase, NAD+, and leucine dehydrogenase.

18. A method of regenerating cell culture media, wherein said media contains ammonia and lactate, said method comprising adding to said cell culture media an amino acid precursor, a first enzyme capable of catalyzing the reaction between ammonia and said amino acid precursor to give an amino acid, a recycling cofactor and a second enzyme capable of regenerating said cofactor and dehydrogenating lactate to give pyruvate.

19. The method of claim 18, wherein said amino acid precursor is selected from the group consisting of α-ketoisocaproate, α-ketoisovalerate, and α-keto-β-methylvalerate.

20. The method of claim 18, wherein said first enzyme is leucine dehydrogenase.

21. The claim of claim 18, wherein said recycling cofactor is NAD+.

22. The method of claim 18, wherein said second enzyme is lactic dehydrogenase.

23. The method of claim 18, further comprising adding to said cell culture system adenosine diphosphate.

24. The method of claim 18, wherein said first and second enzymes are added to said cell culture system in microencapsulated form.

* * * * *